(12) United States Patent
Banko

(10) Patent No.: US 10,709,603 B2
(45) Date of Patent: Jul. 14, 2020

(54) DUAL LUMEN SURGICAL HAND-PIECE WITH ULTRASONIC KNIFE

(71) Applicant: SURGICAL DESIGN CORPORATION, Armonk, NY (US)

(72) Inventor: William Banko, Armonk, NY (US)

(73) Assignee: SURGICAL DESIGN CORPORATION, Armonk, NY (US)

(*) Notice: Subject to any disclaimer, the term of this patent is extended or adjusted under 35 U.S.C. 154(b) by 158 days.

(21) Appl. No.: 15/783,806

(22) Filed: Oct. 13, 2017

(65) Prior Publication Data

US 2019/0117457 A1    Apr. 25, 2019

(51) Int. Cl.
| | | |
|---|---|---|
| A61F 9/007 | (2006.01) | |
| A61M 3/02 | (2006.01) | |
| A61B 17/32 | (2006.01) | |
| A61M 1/00 | (2006.01) | |
| A61F 9/008 | (2006.01) | |

(52) U.S. Cl.
CPC ....... *A61F 9/00745* (2013.01); *A61M 1/0064* (2013.01); *A61B 2017/32007* (2017.08); *A61B 2017/320084* (2013.01); *A61B 2217/005* (2013.01); *A61F 9/008* (2013.01); *A61F 2009/0087* (2013.01); *A61F 2009/00887* (2013.01); *A61M 3/0283* (2013.01); *A61M 2210/0612* (2013.01)

(58) Field of Classification Search
CPC .. A61B 17/320068; A61B 2017/32007; A61B 2017/320074; A61B 2017/320084; A61F 9/00745; A61M 1/0064; A61M 3/0283
See application file for complete search history.

(56) References Cited

U.S. PATENT DOCUMENTS

| | | |
|---|---|---|
| 3,906,954 A | 9/1975 | Baehr et al. |
| 3,976,077 A | 8/1976 | Kerfoot, Jr. |
| 4,320,761 A | 3/1982 | Haddad |
| 4,368,734 A | 1/1983 | Banko |
| 4,504,264 A | 3/1985 | Kelman |

(Continued)

FOREIGN PATENT DOCUMENTS

| | | |
|---|---|---|
| CN | 106175848 A | 12/2016 |
| GB | 2 293 104 A | 3/1996 |
| WO | WO-2017/001379 A2 | 1/2017 |

OTHER PUBLICATIONS

International Search Report and Written Opinion in corresponding PCT Application No. PCT/2018/055193, dated Jan. 7, 2019.

(Continued)

*Primary Examiner* — Ryan J. Severson
(74) *Attorney, Agent, or Firm* — Leason Ellis LLP

(57) ABSTRACT

A surgical hand piece has a solid surgical knife connected to a source of ultrasonic energy. Two or more rigid plastic irrigation and aspiration tubes are provided alongside the knife and they may be supported with respect to the knife by tube holders fastened to the hand piece housing for the source of ultrasonic energy. The rigid plastic tubes may be connected toward their distal ends by a support in the form of bands about the tubes and knife, a sleeve about the tubes and knife or a sleeve about the knife with the tubes supported on the external surface thereof.

22 Claims, 8 Drawing Sheets

(56) References Cited

U.S. PATENT DOCUMENTS

| | | | |
|---|---|---|---|
| 4,998,527 A * | 3/1991 | Meyer | A61B 1/015 600/104 |
| 5,725,495 A * | 3/1998 | Strukel | A61M 1/0043 604/44 |
| 5,741,226 A * | 4/1998 | Strukel | A61M 1/0043 604/35 |
| 5,743,871 A * | 4/1998 | Strukel | A61M 1/0043 604/35 |
| 6,159,175 A * | 12/2000 | Strukel | A61M 1/0043 604/22 |
| 6,299,591 B1 * | 10/2001 | Banko | A61M 1/0043 604/22 |
| 6,592,541 B1 * | 7/2003 | Kurwa | A61F 9/00745 604/22 |
| 7,083,589 B2 | 8/2006 | Banko et al. | |
| 8,348,880 B2 * | 1/2013 | Messerly | A61B 17/320092 604/22 |
| 8,348,967 B2 | 1/2013 | Stulen | |
| 8,641,658 B1 | 2/2014 | Banko | |
| 8,911,460 B2 * | 12/2014 | Neurohr | A61B 17/320068 606/169 |
| 9,211,137 B2 * | 12/2015 | Voic | A61B 17/320068 |
| 9,693,793 B2 * | 7/2017 | Akagane | A61B 18/1402 |
| 9,867,736 B2 * | 1/2018 | Morlet | A61F 9/00745 |
| 10,166,317 B2 * | 1/2019 | Banko | A61B 17/3421 |
| 10,179,068 B2 * | 1/2019 | Banko | A61M 1/0064 |
| 10,207,045 B2 * | 2/2019 | Banko | A61F 9/008 |
| 2003/0114873 A1 * | 6/2003 | Banko | A61F 9/00745 606/169 |
| 2005/0049546 A1 * | 3/2005 | Messerly | A61B 17/320092 604/22 |
| 2008/0234710 A1 | 9/2008 | Neurohr et al. | |
| 2008/0294087 A1 | 11/2008 | Steen et al. | |
| 2009/0030438 A1 * | 1/2009 | Stulen | A61B 17/320068 606/169 |
| 2013/0023918 A1 | 1/2013 | Morlet | |
| 2014/0114335 A1 * | 4/2014 | Banko | A61B 17/3421 606/169 |
| 2014/0276369 A1 * | 9/2014 | Banko | A61M 1/0064 604/22 |
| 2014/0329269 A1 | 11/2014 | Adey et al. | |
| 2015/0025451 A1 | 1/2015 | Banko | |
| 2016/0374707 A1 | 12/2016 | Akagane | |
| 2019/0117253 A1 * | 4/2019 | Banko | A61B 17/320068 |
| 2019/0117456 A1 * | 4/2019 | Banko | A61F 9/00745 |
| 2019/0117457 A1 * | 4/2019 | Banko | A61F 9/00745 |
| 2019/0117458 A1 * | 4/2019 | Banko | A61F 9/00745 |
| 2019/0133822 A1 * | 5/2019 | Banko | A61F 9/00745 |
| 2019/0133823 A1 * | 5/2019 | Banko | A61F 9/00745 |

OTHER PUBLICATIONS

International Preliminary Report on Patentability in corresponding PCT Application No. PCT/US2018/055193, dated Apr. 23, 2020.

* cited by examiner

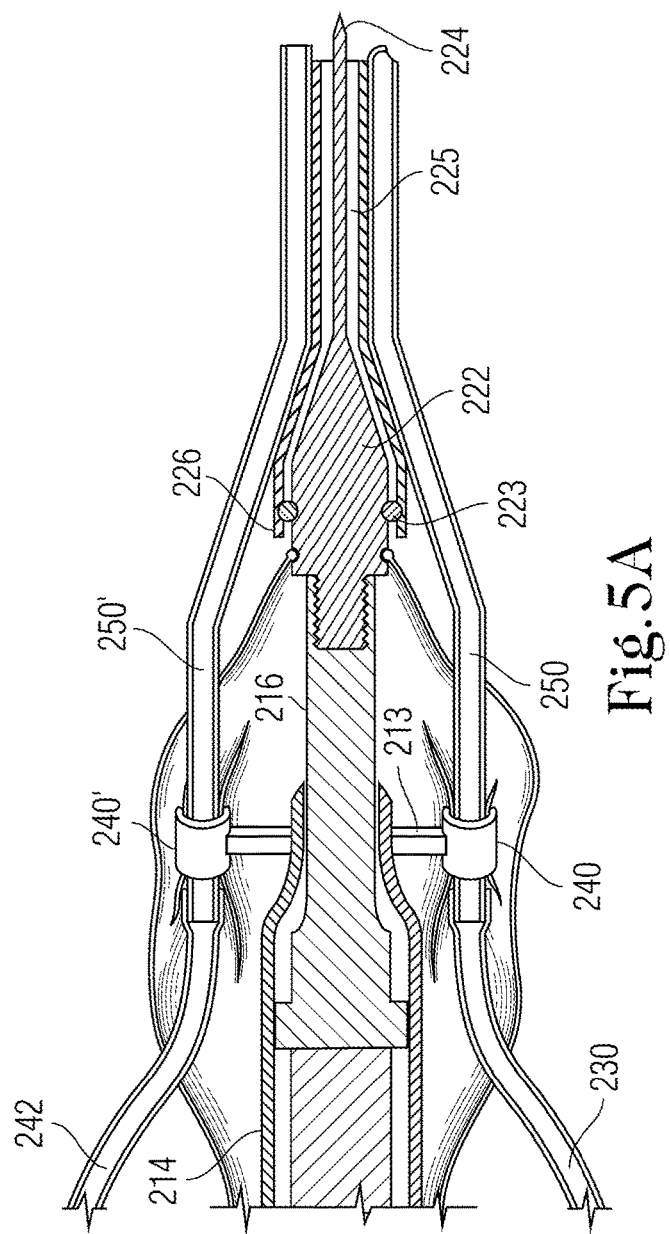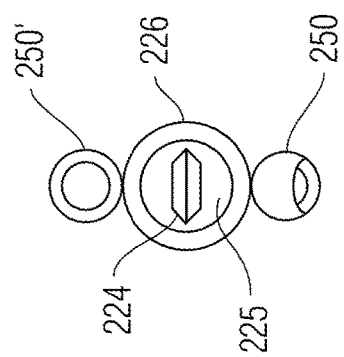

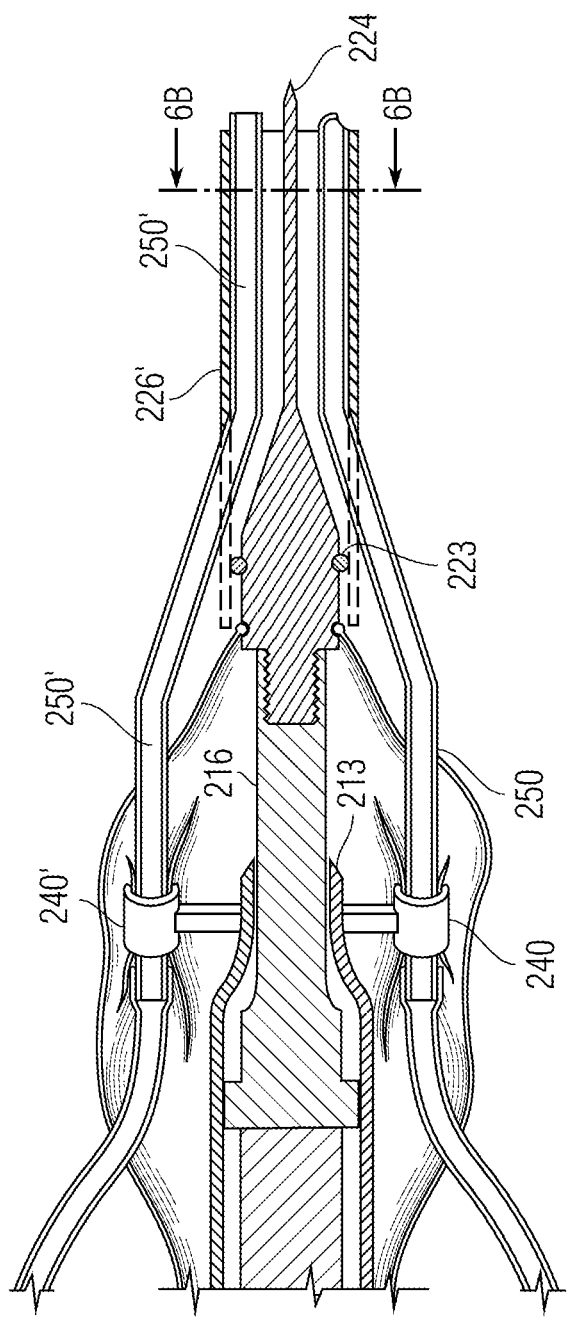
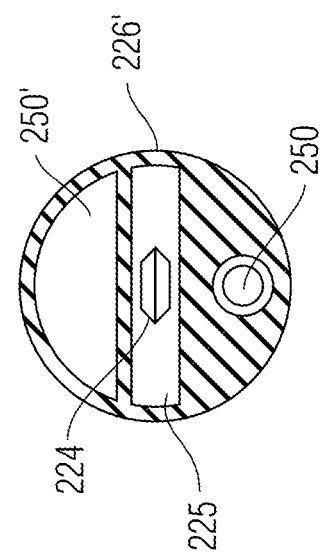
Fig.6A
Fig. 6B

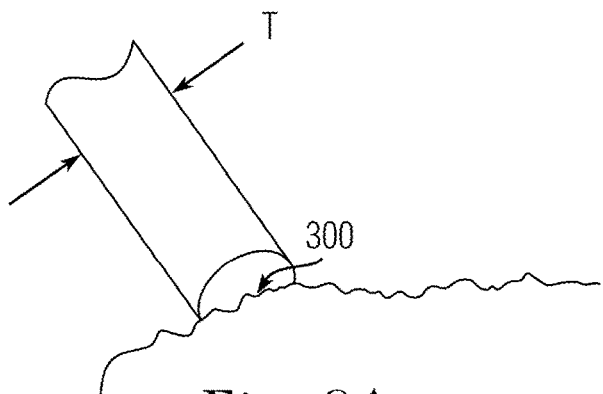
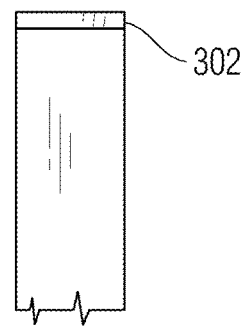
Fig. 8A  Fig. 8B
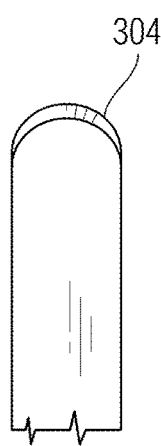 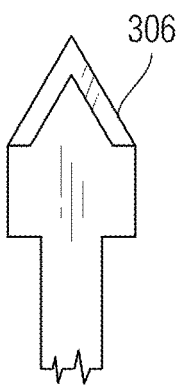 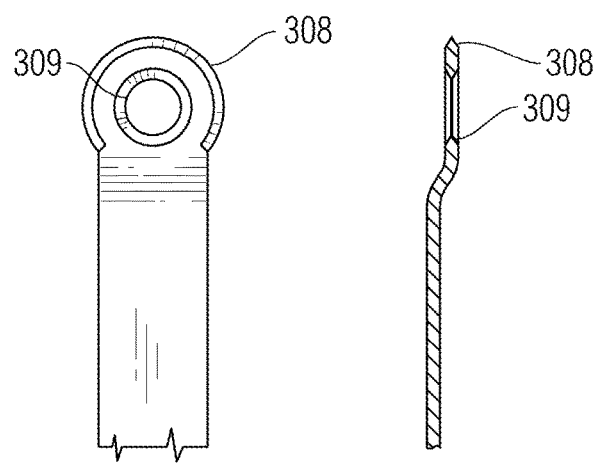
Fig. 8C  Fig. 8D  Fig. 8E  Fig. 8F
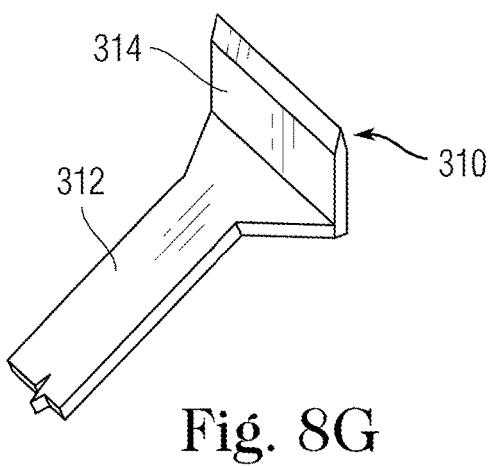 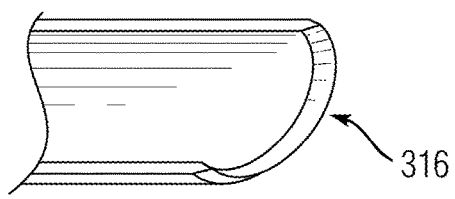
Fig. 8G  Fig. 8H

DUAL LUMEN SURGICAL HAND-PIECE WITH ULTRASONIC KNIFE

TECHNICAL FIELD

The present invention is generally directed to hand pieces for surgery, particularly for the removal of cataracts from the eye of a patient by phacoemulsification.

BACKGROUND OF THE INVENTION

The use of instruments in ocular surgical applications is well known. One widely used type of instrument is an ultrasonic hand piece that is used in ophthalmic applications, such as in the removal of cataracts from the eye by phacoemulsification.

FIG. 1 depicts one such type of prior art ultrasonic hand piece as shown in U.S. Pat. No. 4,504,264 of Kelman. This hand piece has a housing 10 of, for example, plastic or metal, within which is supported a transducer means 11 for generating mechanical vibrations upon excitation with an alternating-current electrical signal. The transducer 11 is shown as a magnetostrictive transducer with an electrical coil 12 wound about a stack of metal laminations so that longitudinal mechanical vibrations are produced. The transducer can also be of the piezoelectric type. There is a connecting body 16 of, for example, titanium, having a reduced diameter distal end portion, which also can be an attached separate portion. The connecting body forms an acoustic impedance transformer for conveying the longitudinal vibrations of the transducer 11 for application to an operative tool or working tip 14 connected to the distal end of the connecting body 16.

The work tip 14 is connected, such as by a screw thread, to the narrowed distal end of the connecting body 16 so as to be coupled to the transducer 11. As a result, the work tip is longitudinally vibrated by the transducer. The working tip 14 is an elongated, hollow tube of a suitable metal, such as titanium, that is capable of supporting ultrasonic vibrations. It has a distal end of a desired shape to be placed against the tissue to be removed. The work tip 14 has a base portion 15 in threaded engagement with the distal end of the connecting body 16. The tip 14 can be interchanged by use of the screw threads.

The distal end of the tube 14 is shown surrounded by a sleeve 17, which may be made of a material such as silicone, whose proximal end 18 is supported in threaded engagement on a reduced diameter end of the housing 10. If desired, the proximal end of sleeve 17 can be engaged more proximally along the length of the housing 10. The connecting body 16 has two elastomeric O-rings 19, 20 on its outer surface. These provide a fluid-tight seal between the connecting body 16 and the transducer means 11. A plurality of screws 51 are shown disposed around the axis of the housing 10 for preventing longitudinal displacement (other than vibration) or rotational movement of the vibratory structure within the housing and also for radial centering of the vibratory structure within the housing. Other types of conventional mounting arrangements can be used.

The hand piece also illustratively has electrical input terminals 40, 41 for applying a suitable electrical signal to the magnetostrictive transducer 11. Cooling water is shown provided inside the housing 10 from an inlet 42 to an outlet 43 and within a chamber between O-ring 19 and a grommet 50 for circulation around the transducer. This is not always necessary and is not used in most present day hand pieces.

The sleeve 17 around the end of tube 14 forms a first fluid passage 21 between the tip 14 and the sleeve for an infusion/irrigation fluid. An inlet 22 is provided on the housing or sleeve distally of the O-ring 20 for supplying the irrigation fluid to the passage 21 from a fluid supply, e.g., a bag of saline solution (not shown).

A passage 23 is formed through the connecting body 16 that is in communication with a central passage 25 of the work tube 14. An outlet 24 on the housing or sleeve receives a suction (aspiration) force that is applied to the passage 23 in the connecting body and the central passage 25 in the work tip tube 14. A chamber 31 is formed between the spaced O-rings 19, 20 on the body 16 and the housing 10, with which the aspiration force from outlet 24 communicates. Thus the aspiration force is from the source (e.g., a suction pump not shown), into the chamber 31 between the O-rings, through the passage 23 in the connecting body and the passage 25 in the work tip 14. Tissue that is emulsified by impact with the work tip tube 14 is aspirated from the operating site by the aspiration flow force through the tube. In particular, saline solution introduced into the eye through fluid passage 21 and tissue displaced by the vibration force of the tube 14, is drawn into the distal end of passage 25 and passes out of the hand piece through outlet 24. It should be noted that passage 25 is located concentrically within passage 21.

Considering now the operation of the hand piece of FIG. 1. When an electrical signal having a frequency of, for example, 40,000 cycles/second is applied to the coil 12 around the magnetostrictive transducer 11, the transducer 11 vibrates longitudinally at 40,000 cycles per second, thereby vibrating the connecting bodies 13, 16 and the work tip tube 14. Treatment fluid is supplied through inlet 22 and fluid passage 21 to bathe the tissue in the operating site region around the working tip tube 14. Suction force is applied through inlet 24 and passage 23 to the working tip tube 14 passage 25 to withdraw the tissue fragmented by the work tip along with some of the treatment fluid.

Instruments of the type described above are often used in cataract surgery in which the eye lens is removed from the eye capsule and an intra-ocular lens (IOL) is then implanted. In such a procedure before the IOL is implanted it has been found to be desirable to cleanup lens substance and lens epithelial cells (LEC's) in the capsular bag of the eye and to remove them. Doing this procedure provides a more stable and long-term fixation for certain types of IOL's in the capsular bag. One manner of accomplishing the cleanup is to use a combination of low force irrigation of the capsular bag interior with a liquid together with the application of low power ultrasonic energy. This dislodges the unwanted cells and substances without damage to the capsular bag. Further, this material can be removed from the capsular bag by the aspiration fluid flow, which also may be reduced in pressure to avoid damage.

In a cleanup procedure it is advantageous if the flow of the irrigation liquid can be made more directional than would be possible using the hand piece with the outer sleeve through which the liquid flows and exits from around the work tip that produces the ultrasonic energy. It is also better if the aspiration force is lower. As a result, typically a different tip from the one illustrated in FIG. 1, which breaks up the tissue, is used for the cleanup. In fact a completely different instrument called an irrigation or infusion/aspiration (I/A) instrument is often used for this purpose. Such an instrument typically has concentric infusion and aspiration lumens, and typically has no ultrasonic vibration capability. The infusion fluid is in an outer concentric lumen so that its flow surrounds the distal part of lumen of the work tip. The aspirated tissue enters a small hole in the distal part and is withdrawn through the central lumen. Thus, when the phacoemulsification has been completed and cleanup is to be started, the surgeon must remove the phacoemulsification tool from the eye. Then the surgeon removes the first or phacoemulsification work tip, replaces it with a different cleanup work tip and then inserts the new work tip or a separate I/A tool is inserted in to the eye. This second insertion into the eye increases the possibilities of infection and trauma. Also, the I/A tool has a disadvantage in that the surgeon would have to keep inserting and withdrawing the ultrasonic work tip and the I/A tool from the eye as the process is completed, because the surgeon cannot be sure that all of the tissue has be broken up until the cleanup process has begun. As a result, this would also subject the patient to the increased possibilities of infection and trauma.

As shown in the present inventor's own U.S. Pat. No. 8,641,658, the surgical instrument may be provided with dual lumens in tubes 132, 134, each of which can alternatively be used for aspiration of emulsified tissue and irrigation of the surgical site. FIG. 2 shows a work tip 130 that can be connected to an ultrasonic energy source 102 of a hand piece by means of a connecting body 204. Two fluid passages 120 and 180 for aspiration or irrigation fluid pass through the connecting body 204. For example the proximal end of passage 120 can be in communication with the irrigation fluid input of the supply line 124 and the proximal end of passage 180 can be in communication with the aspiration fluid of the supply line 164. The distal ends of the two passages 120 and 180 terminate at the distal end of the connecting body 204.

There are threads 182 around the connecting body distal end. A hub 190 is around the proximal ends of the work tip tubes 132 and 134, which are bent so that the proximal ends of their lumens are parallel to the distal ends of the connecting body passages 120 and 180. A collar 194 with internal threads on its open end has its flange end rotatably mounted in a groove 192 in the hub 190. There are mating index pieces, such as mating grooves and ribs or pins (not shown), on the opposing faces of the connecting body 204 distal end and the hub 190 so that the proximal end of the lumen of tube 132 will be aligned with the distal end of connecting body passage 120 and the proximal end of the lumen of tube 134 aligned with the distal end of passage 180.

When the tubes and connecting body are properly aligned the collar 194 is tightened on the connecting body threads 182 and the lumens at the proximal ends of tubes 132 and 134 will be brought into fluid communication with the distal ends of the connecting body passages 120 and 180. O-rings 193 are provided in the connecting body at the distal ends of passages 120 and 180 to make the communications fluid tight.

Both of the tubes 132 and 134 receive the ultrasonic energy from the source 102 (not shown). A valve (not shown) can be used with the hand piece of FIG. 2 to switch the fluid flow from the sources 124 and 164 to the lumens of tubes 132 and 134 of the integrated work tip. Since both tubes 132 and 134 receive ultrasonic energy the emulsification of tissue and its aspiration can take place through either one in addition to each tube being able to supply irrigation liquid through the different types and shapes of openings at the distal ends of the tubes.

The work tip can be used with only an irrigation/aspiration (I/A) function by turning off the source of ultrasonic energy and only supplying the aspiration and irrigation fluids. Thus, the same instrument can be used for the phacoemulsification function while performing irrigation and aspiration as an operation takes place and also only for I/A functions (no or minimal ultrasonic energy is used) useful for cleaning the capsular bag as described above. This eliminates the need for the surgeon changing instruments and also provides the surgeon with a work tip having two tubes with different shape openings available for both aspiration and irrigation.

Only one of the tubes, e.g., 134, can be used as an I/A work tip. In the oval shaped openings 165 along the tube length can be used alone in the eye capsular bag for the substance and cell cleanup procedure described above. The oval shaped openings 165 allow for both good dispersion of the irrigation fluid or a large area for aspiration of cells and substances dislodged by the irrigation liquid.

Since the beginning of phacoemulsification surgery, cataracts have been removed by ultrasonic vibration of a hollow titanium needle or needles. There has never been any other proposal of a way to remove a cataract by ultrasonic vibration, other than by means of a hollow needle. The reason for this is that the end of the needle or tube contacts the tissue directly. Therefore the pieces of tissue are directly in front of the tube end as they are separated and can be easily drawn into the open end of the tube by the aspiration force. However, in order to provide the ultrasonic energy to the tissue, the thin needle must be made of a very strong material. Also the material should be biocompatible. Titanium has been the material of choice.

Titanium, however, is a material that is hard to work with and is expensive. In the early days of phacoemulsification the cost for surgery was high and the expense of the titanium needle was of no great concern. However, as the surgical cost has come down and since there has been increased pressure to reduce medical costs; the cost of the needle has become significant. The expense of titanium and the difficulty of working with it are even more significant with the present inventor's dual lumen work tip as illustrated in U.S. Pat. No. 8,641,658. With this design, not only are there two titanium tubes, but their proximal ends have significant bends that prove to be a manufacturing challenge when titanium is used.

In prior times after a phacoemulsification procedure, the instruments (including the work tip tube) were sterilized for use with another patient. However, as disclosed for example, in the present inventor's U.S. Patent Application Publication No. 2015/0025451 A1 (FIG. 5), the work tip and its supporting hub can now be discarded after each use along with a sterile sheet or bag. This saves the expense of sterilization and speeds up the operation so that more patients can receive the surgery in a single day, thus reducing the cost to each. The problem is that this disposable work tip creates even more impetus to reduce its cost.

SUMMARY OF THE INVENTION

In accordance with the invention a surgical hand piece is provided with a solid ultrasonic knife or scalpel made of titanium alloy or a material that is less expensive and easier to manufacture than titanium. Further, plastic or other inexpensive tubes can be provided next to the knife blade to provide both aspiration and irrigation. Thus, instead of the titanium needle providing emulsification, irrigation and aspiration, these functions are separated according to the present invention. Thus, only the emulsification function is carried out by a metal blade and the other functions can be carried out with less strong and less expensive tubes laid next to the metal blade. Further, the operation of the aspiration and irrigation tubes can be reversed as needed for phacoemulsification and cleanup.

In an illustrative embodiment the surgical hand piece has a solid knife, as opposed to one or more hollow tubes, connected to a source of ultrasonic energy. The vibrating knife may be used for phacoemulsification of cataracts. Aspiration and irrigation tubes made of rigid plastic are located next to, but are separated from the knife. There is a support for holding the tubes together next to the knife.

In one embodiment the support is a series of bands that surround the knife and the tubes. In a second embodiment the support in in the form of a sleeve of hard plastic material with the knife in the interior of the sleeves and the tubes attached to its outer surface. In a third embodiment the knife and at least one of the tubes are in the interior of the sleeve. Also, as an option, efforts are made to isolate the shell from the vibrating blade, e.g., with O-rings between the blade and shell, where the O-rings are made of Teflon. Further, if the embodiments are surrounded by a sterile sheet that is attached to the sterile disposable work tip, the work tip can be a single use disposable product and the handpiece need not be sterilized between uses.

The work piece of the present invention can be used not only in cataract surgery but in general surgery or neurological surgery as well.

The principles of the invention have numerous advantages. For example, the invention allows for a less expensive and easier to manufacture work tip because of the solid knife instead of the single or dual tubes. In addition, the design of the present invention allows the work piece to be used both for phacoemulsification and clean up without having to remove the work piece from the surgical site, such as the eye, and to replace it with an I/A clean up tool. Further, according to the present invention, clean up can be commenced without the surgeon having to divert his attention from the eye of the patient.

BRIEF DESCRIPTION OF THE DRAWINGS

The foregoing and other objects and advantages of the present invention will become more apparent when considered in connection with the following detailed description and appended drawings in which like designations denote like elements in the various views, and wherein:

FIG. 5A is a cross-sectional fully assembled view of a surgical hand piece according to a second exemplary embodiment of the present invention and FIG. 5B is an end view of the work tip of the embodiment of FIG. 5A;

FIG. 6A is a cross-sectional fully assembled view of a surgical hand piece according to a third exemplary embodiment of the present invention and FIG. 6B is an end view of the work tip of the embodiment of FIG. 6A;

FIG. 8A is perspective view of a prior art tube shaped work tip sculpting cataract tissue, FIG. 8B is a top view of a knife according to the present invention, FIG. 8C is a top view of a first alternative knife with a curved shape, FIG. 8D is a top view of a second alternative knife with a tapered shape, FIG. 8E is a top view of a third alternative knife with a round cutting edge and an aperture cutting edge, FIG. 8F is a side view of the knife of FIG. 8E, FIG. 8G is a top view of a fourth alternative knife with a rake shape; and FIG. 8H shows a half tube-shaped blade.

DETAILED DESCRIPTION OF THE INVENTION

Figure 3:
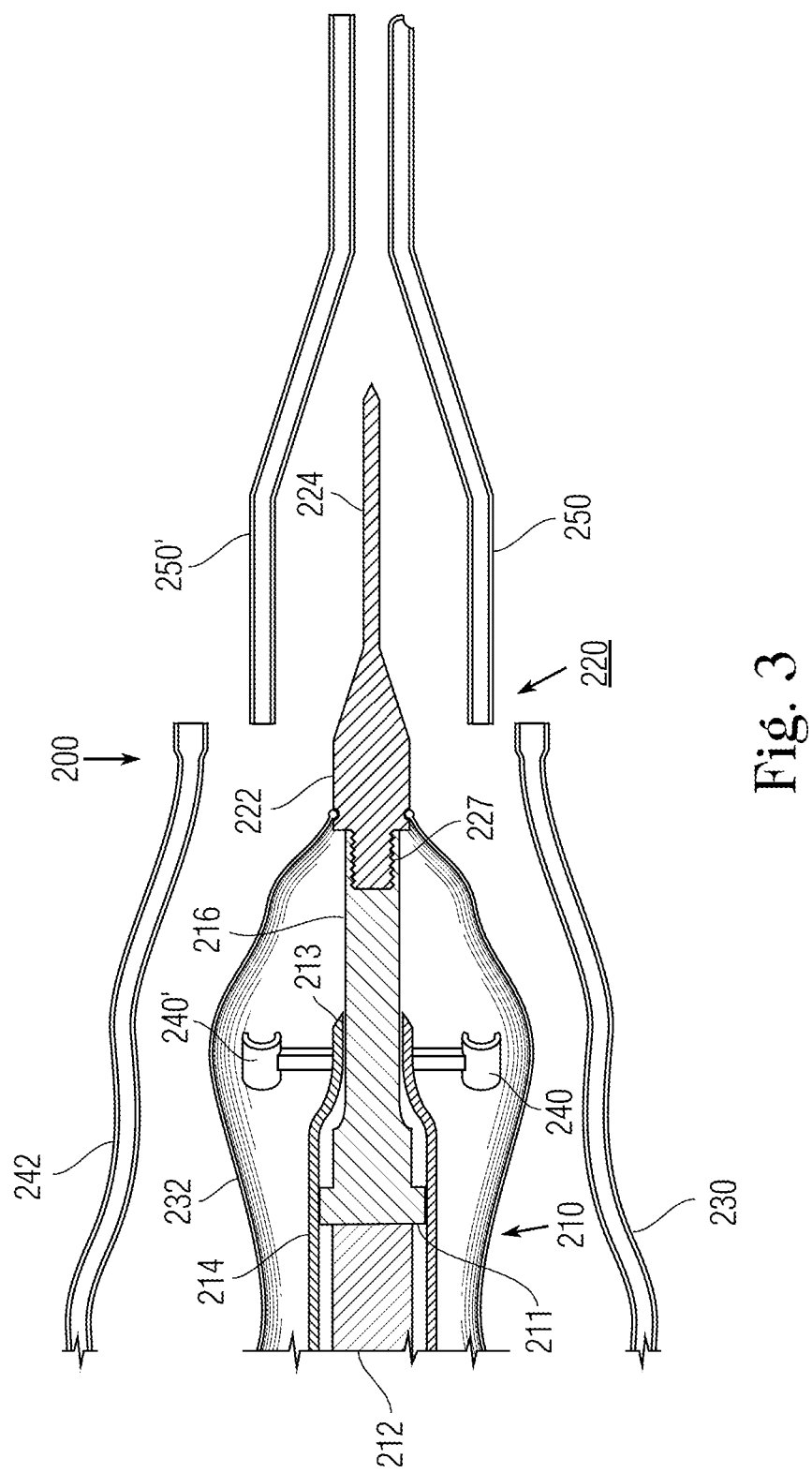
FIG. 3 is a cross-sectional exploded view of a surgical hand piece according to a first exemplary embodiment of the present invention.

FIG. 3 shows an exploded view of a handpiece 200 according to an illustrative first embodiment of the present invention. This hand piece has an ultrasonic vibration part 210 connected to a disposable work piece 220. The vibration part has a housing 214. A transducer 212 is provided in part 210 for generating ultrasonic linear mechanical vibrations upon excitation with an alternating-current electrical signal. The transducer is supported within the housing 210 by flanges 211. A metal connecting body 216 having a reduced diameter distal end portion is attached to the transducer 212. The connecting body forms an acoustic impedance transformer for conveying the longitudinal vibrations of the transducer 212 for application to the operative working tip 220 connected to the distal end of the connecting body 216. Further, the housing has a part 213 that engages the connecting body 216 at a null point in its vibration to provide further support.

The work tip 220 has a hub 222. In an illustrative embodiment a proximal end of the hub 222 has threads 227 that connect to threads in the distal end of the connecting body 216. The distal end of the hub narrows down to form a solid knife or scalpel 224. Flexible tube 230 extracts aspiration fluid from a rigid plastic tube 250 that is located along the knife 224 in the assembled condition. Similarly a flexible tube 242 provides irrigation fluid to a rigid plastic tube 250' that is located along the knife 224. The tubes may be made of polysulfone.

A sterile sheet 232 surrounds the vibration part 210 to isolate it from the non-sterile conditions at the work tip 220. In this design the sheet 232 is attached to the hub 222 of the knife which is detachable from the connecting piece 216. As a result, after an operation the hub can be detached from the work piece and it, the knife and the sheet can be discarded as a one use product. Since the vibration part 210 did not come into contact with any tissue or fluids from the last patient, and will not contact the tissue or fluids from the next patient, there is no need to sterilize the vibration part between operations on different patients. As a result, multiple operations can be conducted in a shorter period of time and at less expense.

Figure 4A:
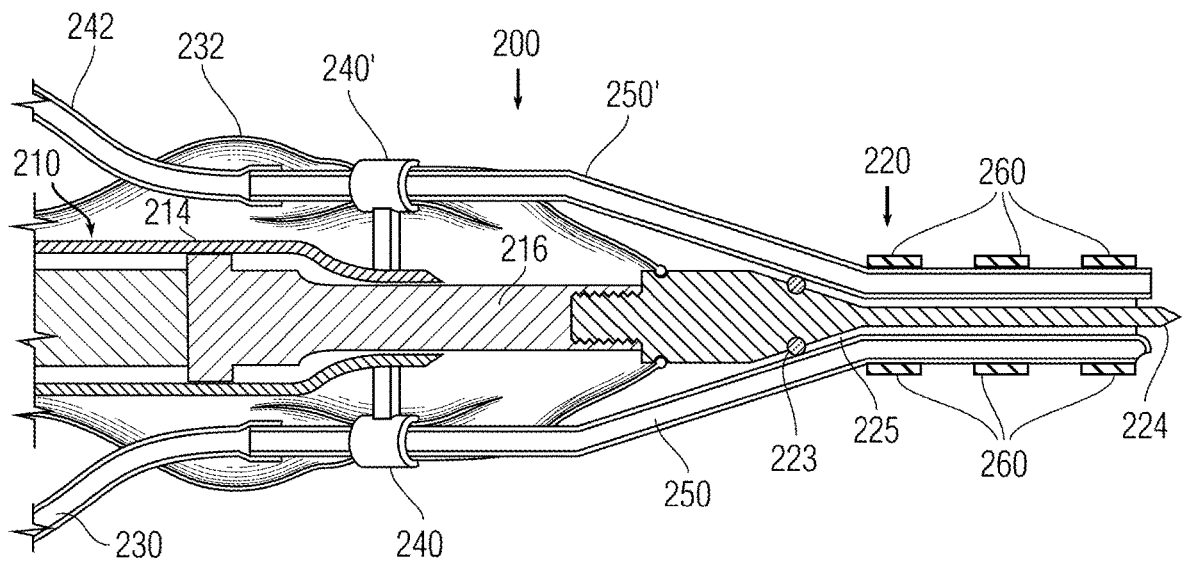
FIG. 4A is a cross-sectional fully assembled view of a surgical hand piece according to the first exemplary embodiment of the present invention.
Figure 4B:
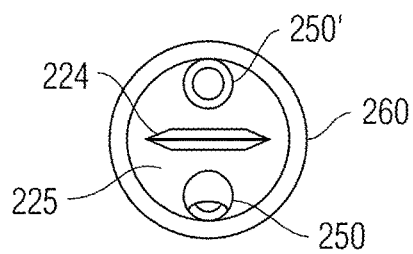
FIG. 4B is an end view of the work tip of the embodiment of FIG. 4A
Figure 4C:
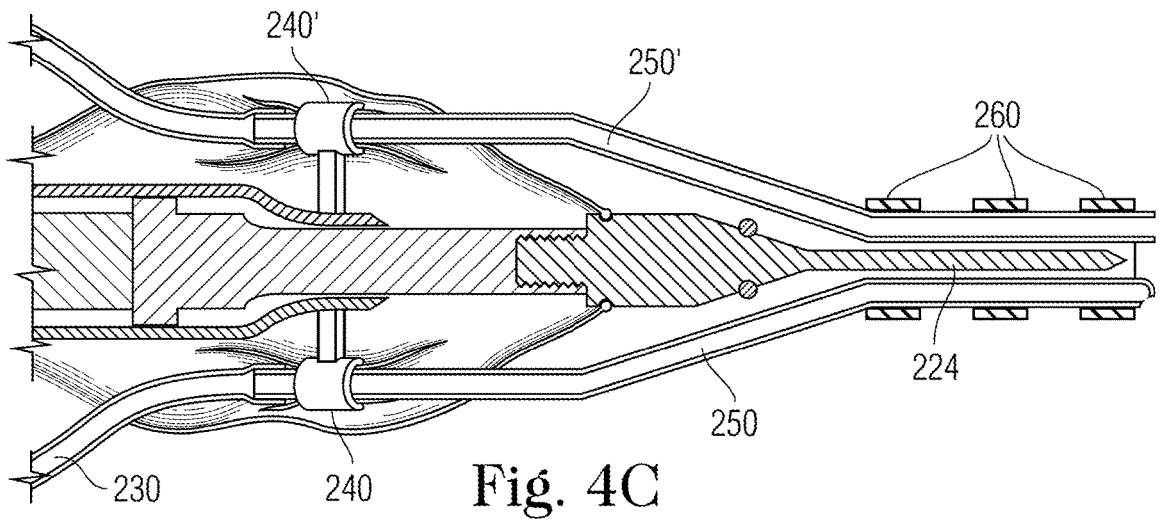
FIG. 4C shows the embodiment in the position for cleanup with the tubes extended beyond the knife.

As shown in the assembled condition in FIG. 4A, rigid tubes 250, 250' are captured in tube holders 240, 240' with the sterile sheet between them. That is, the holders are within the sheet and are not exposed to the operating environment. The knife is slid between the plastic tubes 250, 250' so the knife is adjacent to the tubes, but does not touch them. The tubes and knife are held together by bands 260 that surround their distal end at one or more locations. Three bands are shown in FIG. 4A. The arrangement of the first band 260, the tubes 205, 250' and the knife 224 is best seen in the end view of FIG. 4B.

During an operation, the hub 222 and knife 224 of work tip 220 are longitudinally vibrated by the transducer 212. The tubes 250, 250' are supported with respect to the hub and knife by means of an O-ring 223 at the interface between the hub and the tubes. This O-ring also keeps fluid from the surgical site from traveling along the knife an exiting the work tip beyond the hub. The surgeon places the work tip 220 within the eye and against the cataract tissue. The ultrasonic vibration of the knife 224 causes the cataract tissue to emulsify. During this process irrigation fluid, e.g., saline solution is injected into the site from tube 250' since flexible tube 242 is connected to a source of irrigation fluid which may be moved by gravity flow or a pump. Also, the emulsified tissue is removed from the site by aspiration through tube 250 because flexible tube 230 is attached to an aspiration pump.

Figure 1:
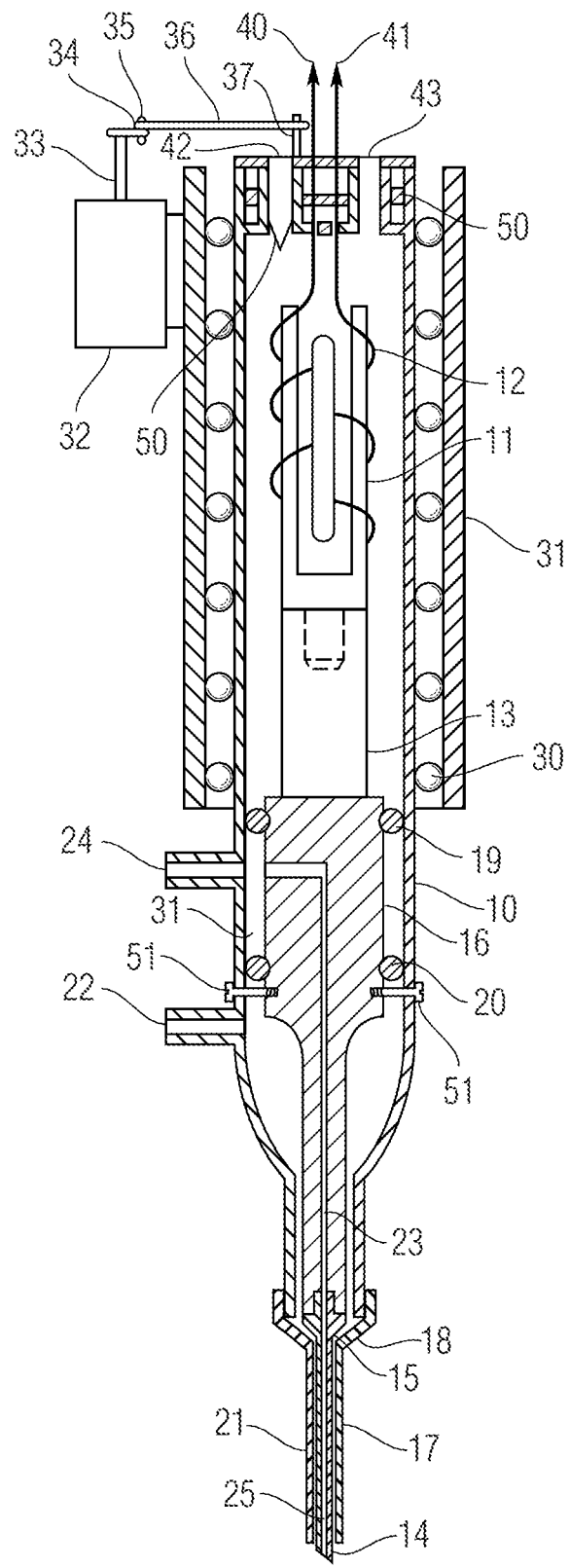
FIG. 1 is a view in partial cross-section of a prior art type of surgical hand piece.
Figure 2:
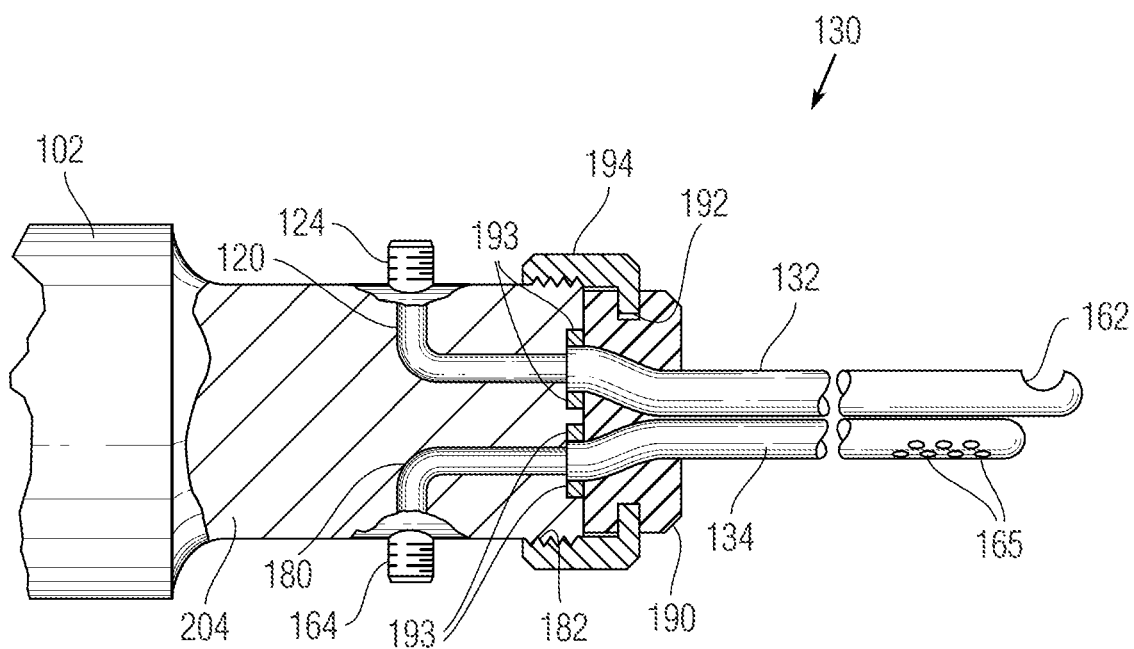
FIG. 2. is cross-sectional view of a prior art dual lumen surgical hand piece.

It should be noted that the function of tubes 230, 250 and 242, 250' can be switch as regards irrigation or aspiration at the choice of the surgeon. After a phacoemulsification operation their still remain isolated bits of lens substance and lens epithelial cells. These need to be cleaned up without rupturing the capsular bag. Typically this is done by removing the phacoemulsification tool and replacing it with an infusion/aspiration (I/A) clean up tool. Such I/A tools have smaller aspiration openings so as not to trap ocular tissue as the fluid is sucked out. Also they are operated al lower pressure and typically without ultrasonic vibration. This switching of tools can delay the procedure and provide the opportunity for contamination and irritation of the eye. One aspect of the present invention is that the irrigation and aspiration force of the hand piece can be lowered and the vibration stopped. The tips of the irrigation and aspiration tubes can be designed with shapes that allow clean up by switching their operation much like the ends 162 and 165 of the prior art device shown in FIG. 2.

One of the important features of the present invention is that the knife or scalpel 224 is made of solid material, as opposed to the elongated, hollow titanium alloy tube of the prior art. Such a solid blade may have been used in other surgical tools, but it has not been used previously in the removal of cataracts by phacoemulsification. Since the knife has a diameter about the size of the hollow tubes used in the prior art, it is much stronger than those tubes if made of the same material, i.e., a titanium alloy. As a result, the knife can be made thinner than the prior art tubes. As an alternative the blade can be made of a weaker material, e.g., surgical stainless steel (type 316L), than the titanium alloy of the prior tubes. Making the blade thinner may not be a good choice because it may lead to bending.

Titanium alloy (Grade 2) is stronger and lighter in weight than surgical stainless steel (type 316L). However, Titanium is about three times the cost. See the article, Young et al, "Titanium is not too Expensive," http://c.ymedn.com/sites/www.titanium.org/resource/resmgr/2010 . . . /YoungChuck_2012.pdf. Further, many of titanium's material and component design characteristics make it expensive to machine. A considerable amount of stock must be removed from primary forms such as forgings, plates, bars, etc. In some instance, as much as 50 to 90% of the primary form's weight ends up as chips. See the article "Machining Titanium and Its Alloys," http://www.jobshop.com/techinfo/papers/machiningtitanium.shtml. Another choice is to make the knife by casting a hard ceramic material. This avoids the need to machine the material as is typically done with titanium. By making the solid blade 224 of a less expensive and more easily machined material, the overall cost of the disposable product is reduced.

As a second embodiment and as shown in FIG. 5A, the bands 260 can be replaced with a plastic sleeve 226 that surrounds the hub and knife. Its proximal end is larger to accommodate the hub. This larger end is reduced in size toward its distal end so as to form about the knife. As a result, a relatively uniform channel 225 is created between the inner surface of the outer shell 226 and the combination hub and knife. The channel 225 extends from the distal end of the work piece 220, but is blocked by O-ring 223 at the end of the sleeve 226. This O-ring also keeps fluid from the surgical site from traveling along the knife and exiting the work tip beyond the hub. Also, it tends to isolate the vibration of the knife from the structure of the tubes 250, 250'. Basically the tube holders 240, 240' are fastened to the housing 214, which is stationary. Therefore the holders are relatively stable. The holders engage rigid tubes 250, 250' so they are stable with respect to the knife which is vibrating. The support of the rigid tubes by the holders is cantilevered. In order to augment this support, the tubes may contact sleeve 226, which because of O-rings 223 receive only reduced vibration from hub 222.

As best seen in FIG. 5B the tubes 250, 250' are affixed to the outer surface of the sleeve 226. Other than replacing the bands 260 with the sleeve 226, the operation of the first and second embodiments are similar.

A third embodiment shown in FIG. 6A has tubes 250, 250' located inside a sleeve 226'. These tubes penetrate the sleeve distal of an O-ring 223. Rather than being circular, like that in FIG. 5A, the tube 250' inside the sleeve 226' has a semicircular shape. On the other hand, tube 250 has a circular shape. Both of these tubes are on opposite sides a channel 225 in which the vibration knife is located. As with the design of FIG. 5A, the proximal end of channel 225 is blocked by O-ring 223.

Figure 7A:
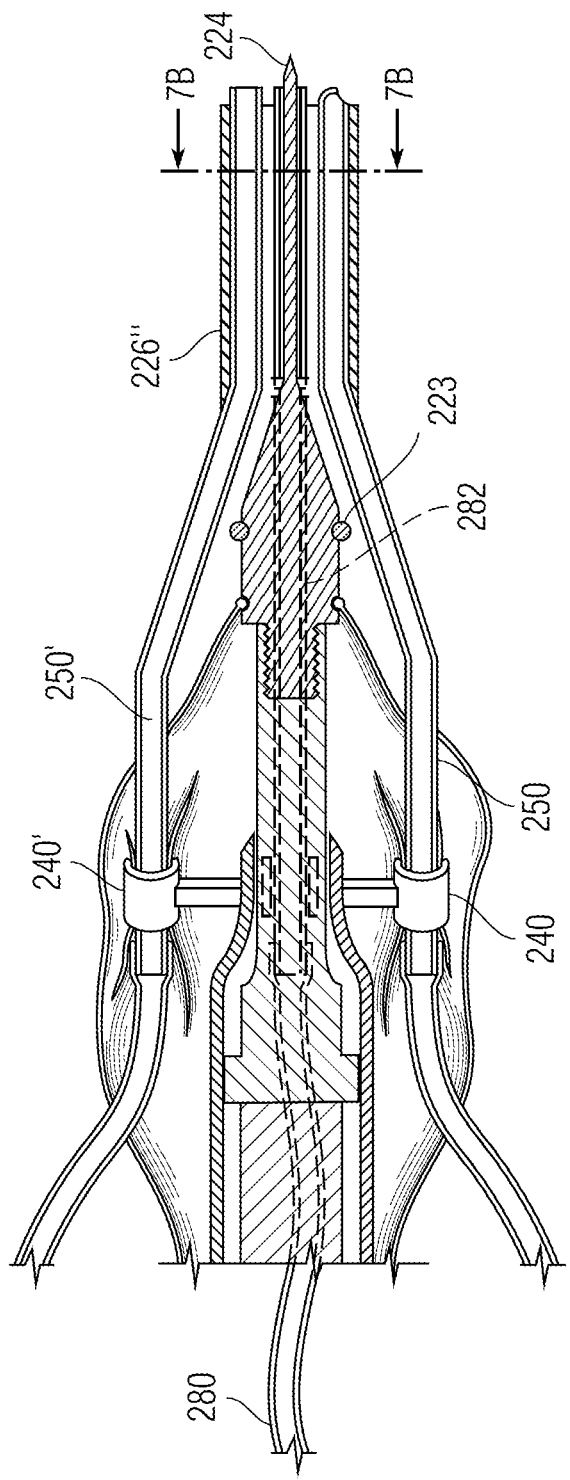
FIG. 7A is a side view of a surgical hand piece according to a fourth exemplary embodiment of the present invention with a third tube and FIG. 7B is an end view of the work tip of the embodiment of FIG. 7A.
Figure 7B:
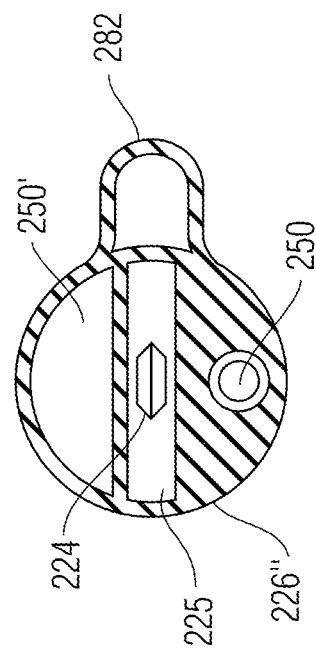

A fourth embodiment is shown in perspective view in FIG. 7A. This embodiment differs from the others in that it includes a third tube 282 that is located on the side of the work pieces while the irrigation tube 250' is on the top and aspiration tube 250 is on the bottom as shown in FIG. 7B. The tubes are all located on a sleeve 226". As with the other designs, the blade is in a channel 225 whose proximal end is blocked by an O-ring 223.

With the design of the fourth embodiment, the extra tube 282 is connected to an aspiration supply. Thus, during phacoemulsification, both tubes 250 and 282 aspirate tissue. During clean up, only tube 250 may be used for aspiration. As an alternative, tubes 250 and 282 may be used for irrigation and tube 250' for aspiration.

As shown in FIG. 8A, a typical prior art tubular phacoemulsification needle has a diameter T of about 0.0480 inches. The knife blades of the present invention have about the same width. During normal operation the tube is used to sculpt the cataract issue, i.e., to shave off pieces. Thus, less than half of the bottom edge 300 of the circular tube contacts and breaks up the tissue. A flat blade of the type shown in FIG. 8B is more efficient because its entire cutting edge 302 can engage the tissue. The blade in FIG. 8C is similar to that in FIG. 8B, but is has a curved cutting edge 304. The blade in FIG. 8D has a pointed blade with two cutting edges. This gives the surgeon a choice of edges with which to contact the tissue. These are essentially one dimensional knives.

FIGS. 8E and 8F show a top and side view of an alternative knife which has a semicircular cutting edge 308. It also has an aperture with an auxiliary cutting edge 309 which can be used with a scraping action. As seen in FIG. 8F the cutting edges are on a lower level than the rest of the knife. This enhances the ability to use the knife with a scraping motion. This is a two dimensional knife.

FIG. 8G relates to a knife that has a flat portion 312 connected to another portion 314 that is perpendicular to the flat portion. The upper edge of the perpendicular portion has a cutting edge 310. It is envisioned that this knife would be dragged across the tissue.

FIG. 8H shows a half tube-shaped blade with a cutting edge 316. It is essentially the functional part of the prior art full tube phacoemulsification needle. A benefit of this design is that it allows the surgeon to utilize surgical techniques previously developed, e.g., channeling and splitting the lens, which should make the surgeon more comfortable in adopting the present invention.

While the invention has been shown and described in connection with the removal of a cataract from the eye of a patient and subsequent I/A clean up, the apparatus and method may also be used for other types of surgery in other parts of the body, e.g., the removal of neurological tissue.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the scope of the appended claims.

I claim:

1. A surgical hand piece comprising:
   a solid knife connected to a source of ultrasonic energy, said knife being a blade that tapers to form a sharp forward cutting edge;
   a housing for the ultrasonic energy source;
   at least one rigid irrigation tube fastened by a tube holder to the exterior of the housing near the proximal end of the irrigation tube and said irrigation tube extends to a distal end thereof along and adjacent the solid knife; and
   at least one rigid aspiration tube fastened by a tube holder to the exterior of the housing near the proximal end of the aspiration tube and said aspiration tube extends to a distal end thereof along and adjacent the solid knife.

2. The surgical hand piece according to claim 1 further including a support located only toward the distal ends of the irrigation and aspiration tubes for stabilizing the tubes with respect to each other.

3. The surgical hand piece according to claim 2 wherein the support is at least one band surrounding the tubes and attached to them.

4. The surgical hand piece according to claim 2 wherein the support is a sleeve surrounding the knife, said tubes being attached to an exterior surface of the sleeve.

5. The surgical hand piece according to claim 2 wherein the support is a sleeve surrounding the tubes and knife with the tubes being attached to the interior of the sleeve.

6. The surgical hand piece according to claim 2 further including an additional support for holding the tubes with respect to the knife, wherein the additional support reduces any transfer of vibration from the knife to the tubes.

7. The surgical hand piece according to claim 6 wherein the additional support is at least one O-ring.

8. The surgical hand piece according to claim 1 further including an additional rigid fluid tube fastened near its proximal end to the housing and extending to a distal end along and adjacent the solid knife.

9. The surgical hand piece according to claim 8 wherein the additional rigid fluid tube is an aspiration fluid tube.

10. The surgical hand piece according to claim 1 wherein, when using the hand piece for clean-up, the rigid irrigation and aspiration tubes can be slid toward the distal end so that the knife is less distal than the sleeves and cannot contact tissue.

11. The surgical hand piece according to claim 1 wherein the knife has a flat blade in top view with a sharp forward edge.

12. The surgical hand piece according to claim 1 wherein the knife has a flat blade in top view with a curved sharp forward edge.

13. The surgical hand piece according to claim 1 wherein the knife has a flat blade in top view with two sharp forward edges at an angle to each other.

14. The surgical hand piece according to claim 1 wherein the knife in top view has a semicircular sharp forward edge and an aperture toward its distal end with sharp edges, said distal end being offset from the rest of the blade.

15. The surgical hand piece according to claim 1 wherein the knife has a flat portion connected to another portion that is perpendicular to the flat portion, and upper edge of the perpendicular portion having a sharp cutting edge.

16. The surgical hand piece according to claim 1 wherein the knife has a half-tube shape with a sharp cutting edge at the distal end.

17. The surgical hand piece according to claim 1 wherein the distal ends of the tubes have openings of different sizes and/or shapes.

18. The surgical hand piece according to claim 17 wherein the opening at the distal end of an aspiration tube is on the side of the tube.

19. The surgical hand piece according to claim 1 wherein the tube holders include a housing portion that is fastened to the exterior of the housing and a gripping portion that forms a clamp for partially surrounding the tubes.

20. The surgical hand piece according to claim 19 wherein the knife has an enlarged hub at its proximal end and further including a flexible bag attached to the hub, surrounding the housing for the ultrasonic energy source and being retained in the clamp of the tube holders.

21. The surgical hand piece according to claim 20 wherein the bag, knife and tubes are sterile.

22. The surgical hand piece according to claim 20 wherein the bag, knife and tubes form a single use disposable unit.

* * * * *